United States Patent
Austin et al.

(10) Patent No.: US 10,470,890 B2
(45) Date of Patent: Nov. 12, 2019

(54) TITANIUM PLASMA COATED MEDICAL GRADE THERMOPLASTIC OR POLYMER PROXIMAL AND DISTAL INTERPHALANGEAL TOE IMPLANT

(71) Applicant: Neutin Orthopedics, LLC, Millersville, MD (US)

(72) Inventors: Albert Eugene Austin, Millersville, MD (US); Steven Keith Neufeld, Washington, DC (US); Adam D. McQueen, Powder Springs, GA (US); Simon J. Mest, Mechanicsville, VA (US); Paul S. Cooper, Potomac, MD (US)

(73) Assignee: Neutin Orthopedics, LLC, Millersville, MD (US)

( * ) Notice: Subject to any disclaimer, the term of this patent is extended or adjusted under 35 U.S.C. 154(b) by 0 days.

(21) Appl. No.: 15/785,339

(22) Filed: Oct. 16, 2017

(65) Prior Publication Data
US 2018/0049881 A1    Feb. 22, 2018

Related U.S. Application Data

(63) Continuation-in-part of application No. 14/825,082, filed on Aug. 12, 2015, now abandoned.
(Continued)

(51) Int. Cl.
*A61F 2/42* (2006.01)
*A61B 17/86* (2006.01)
(Continued)

(52) U.S. Cl.
CPC ........ *A61F 2/4225* (2013.01); *A61B 17/7291* (2013.01); *A61B 17/864* (2013.01);
(Continued)

(58) Field of Classification Search
CPC .................. A61F 2002/4228; A61F 2002/423
See application file for complete search history.

(56) References Cited

U.S. PATENT DOCUMENTS

| | | | |
|---|---|---|---|
| 9,005,648 B2 * | 4/2015 | Jin | A61K 31/7088 424/422 |
| 2011/0257755 A1 * | 10/2011 | Bellemere | A61F 2/4241 623/21.15 |

(Continued)

OTHER PUBLICATIONS

Barkarmo et al., "Enhanced bone healing around nanohydroxyapatite-coated polyetheretherketone implants: An experimental study in rabbit bone", Journal of Biomaterials Applications, 2014, vol. 29(5), p. 737-747.
(Continued)

*Primary Examiner* — Megan Y Wolf
(74) *Attorney, Agent, or Firm* — Potomac Law Group, PLLC; Mark A. Catan

(57) ABSTRACT

A medical grade thermoplastic or polymer implant with an osteoconductive coating is provided, specifically for corrections of the distal and proximal interphalangeal toe joints of the foot. The implant can be either straight or angled, and can be either solid or cannulated for insertion. The implant is sized and shaped depending on the specific anatomy and desired correction. End portions of the implant may be coated with an osteoconductive coating that promotes bone growth, but may reduce radiolucency. Thus, a central portion of the implant may remain uncoated to increase radiolucency of the implant at the region where two bones come together.

15 Claims, 8 Drawing Sheets

Related U.S. Application Data

(60) Provisional application No. 62/284,398, filed on Aug. 12, 2014.

(51) Int. Cl.
| | | |
|---|---|---|
| *A61F 2/30* | (2006.01) | |
| *A61L 27/18* | (2006.01) | |
| *A61L 27/30* | (2006.01) | |
| *A61B 17/72* | (2006.01) | |
| *A61B 90/00* | (2016.01) | |
| *A61B 17/00* | (2006.01) | |

(52) U.S. Cl.
CPC ........ *A61B 17/866* (2013.01); *A61B 17/8625* (2013.01); *A61F 2/30771* (2013.01); *A61L 27/18* (2013.01); *A61L 27/306* (2013.01); *A61B 2017/0092* (2013.01); *A61B 2017/00893* (2013.01); *A61B 2017/00955* (2013.01); *A61B 2090/3966* (2016.02); *A61F 2002/3008* (2013.01); *A61F 2002/3009* (2013.01); *A61F 2002/30065* (2013.01); *A61F 2002/3085* (2013.01); *A61F 2002/3093* (2013.01); *A61F 2002/30327* (2013.01); *A61F 2002/30593* (2013.01); *A61F 2002/30622* (2013.01); *A61F 2002/30841* (2013.01); *A61F 2002/423* (2013.01); *A61F 2002/4228* (2013.01); *A61F 2002/4233* (2013.01); *A61F 2002/4246* (2013.01); *A61F 2002/4248* (2013.01); *A61F 2310/00407* (2013.01); *A61F 2310/00796* (2013.01); *A61L 2430/24* (2013.01)

(56) References Cited

U.S. PATENT DOCUMENTS

| | | | | |
|---|---|---|---|---|
| 2013/0131822 A1* | 5/2013 | Lewis | ............... | A61F 2/4606 623/21.19 |
| 2013/0274814 A1* | 10/2013 | Weiner | ............... | A61B 17/68 606/301 |
| 2014/0188238 A1* | 7/2014 | Sander | ............... | A61F 2/4241 623/21.19 |
| 2015/0142066 A1* | 5/2015 | Shemwell | ......... | A61B 17/7291 606/301 |
| 2016/0310188 A1* | 10/2016 | Marino | ............... | A61F 2/28 |
| 2017/0181785 A1* | 6/2017 | Beyar | ............... | A61B 17/866 |

OTHER PUBLICATIONS

Chadwick et al., "Hammertoes/Clawtoes: metatarsophalangeal joint correction", Foot Ankle Clin., 2011, p. 559-571.

Devine et al., "Coating of carbon fiber-reinforced polyetheretherketone implants with titanium to improve bone apposition", J Biomed Mater Res B, 2013, p. 591-598.

Eagan et al., "A practical correction of great toe claw deformity", J Foot Ankle Surg. 52, 2013, p. 495-497.

Ellington, "Hammertoes and Clawtoes: Proximal Interphalangeal Joint Correction", Foot Ankle Clin N AM 16 (2001) p. 547-558.

Gutteck et al., "Correction arthrodesis of the proximal interphalangeal joint with wire cerclage for rigid small toe deformities. A prospective study", Orthopade. Dec. 2012;41(12); p. 984-8.[Article in German, English Abstract].

Hsu et al., "Complications of Kwire Fixation in procedures involving the hand and wrist", Journal Hand Surgery, 2011, vol. 36A, p. 610-616.

Klammer et al., "Early Complications and Recurrence Rates After Kirschner Wire Transfixion in Lesser Toe Surgery: A Prospective Randomized Study", Foot & Ankle International, vol. 33, No. 2, Feb. 2012, p. 105-112.

Kwon et al., "The Use of Flexor to Extensor Transfers for the Correction of the Flexible Hammer Toe Deformity", Foot Ankle Clin. Dec. 2011;16(4), p. 573-582.

Ma et al., "Current Strategies to Improve the Bioactivity of PEEK", International Journal of Molecular Sciences, 2014;15(4), p. 5426-45.

Poulsson et al., "Osseointegration of machined, injection moulded and oxygen plasma modified PEEK implants in a sheep model", Biomaterials 35 (2014) p. 3717-28.

Rao et al., "Spine interbody implants: material selection and modification, functionalization and bioactivation of surfaces to improve osseointegration", Orthop Surg. May 2014;6(2), p. 81-89.

Rosenthal et al., "Polyetheretherketone Implants for the Repair of Large Cranial Defects—A 3-Center Experience", Neurosurgery. 2014, vol. 75, No. 5, p. 523-529.

Sandhu et al., "Digital Arthrodesis With a One-Piece Memory Nitinol Intramedullary Fixation Device: A Retrospective Review", Foot Ankle Spec. Oct. 2013;6(5): p. 364-6.

Scholl et al., "Smart toe® implant versus buried Kirschner wire for proximal interphalangeal joint arthrodesis: a comparative study", J Foot Ankle Surg. Sep.-Oct. 2013;52(5), p. 580-3.

Unsdorfer et al., "Proximal Phalangeal Osteotomy with Proximal Interphalangeal Joint Arthrodesis for Multiplanar Deformities of the Second Toe: Historical Perspectivesand Review of a Case Series", The Journal of Foot and Ankle Surgery 50 (2011) p. 687-694.

Waser-Althaus et al., "Differentiation of human mesenchymal stem cells on plasma-treated polyetheretherketone", J Mater Sci Mater Med. Feb. 2014;25(2), p. 515-525.

Zelen et al., "Digital arthrodesis", Clin Podiatr Med Surg. Jul. 2013;30(3), p. 271-282.

Zhao et al., "Cytocompatibility, osseointegration, and bioactivity of three-dimensional porous and nanostructured network on polyetheretherketone", Biomaterials. Dec. 2013;34(37), p. 9264-77.

* cited by examiner

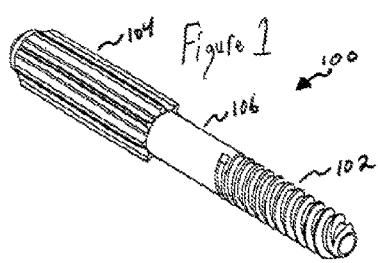
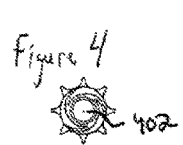
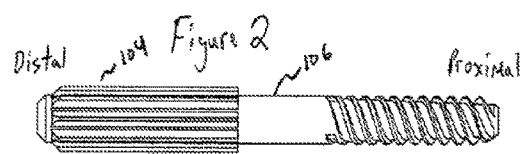
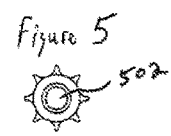
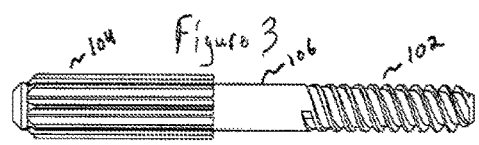

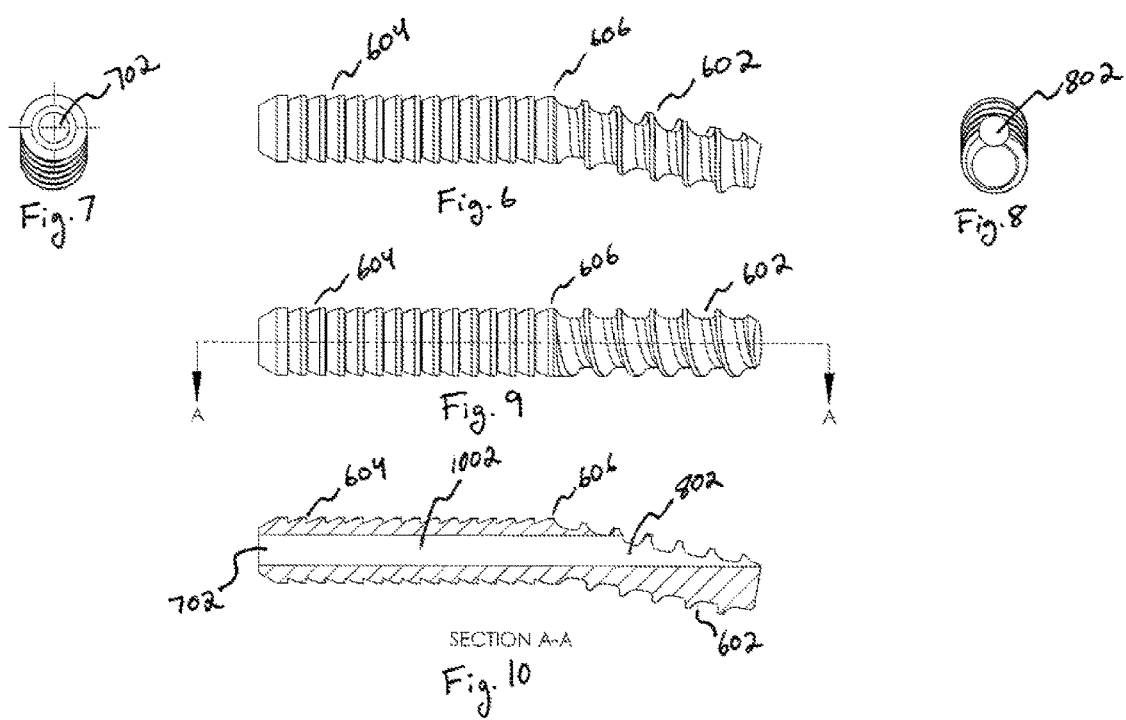

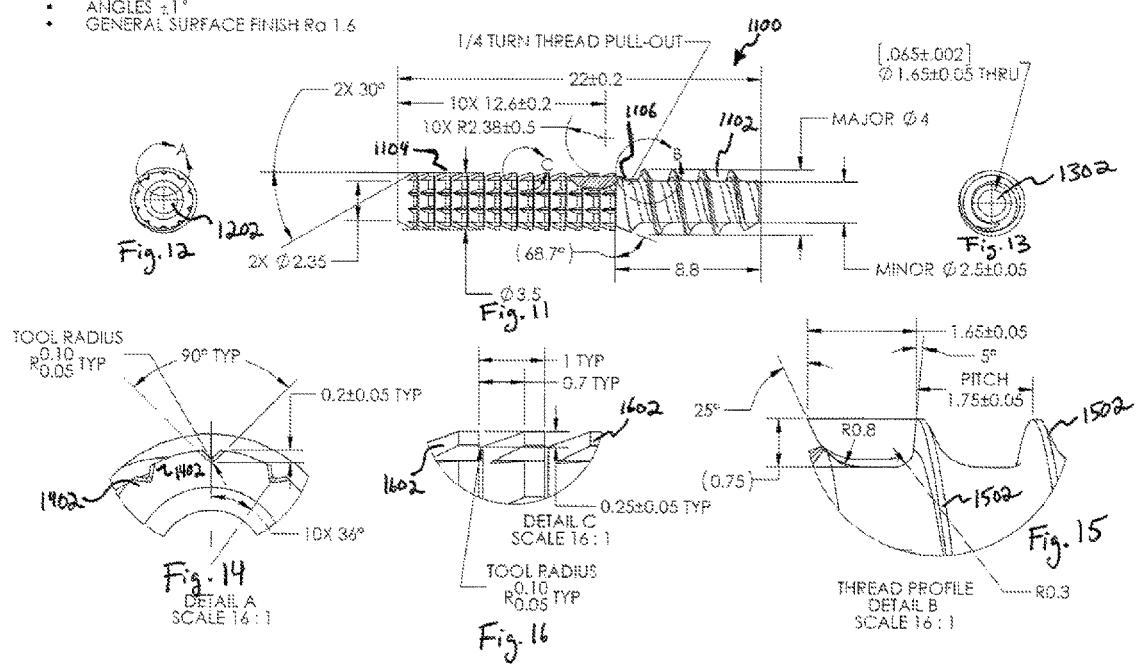

TITANIUM PLASMA COATED MEDICAL GRADE THERMOPLASTIC OR POLYMER PROXIMAL AND DISTAL INTERPHALANGEAL TOE IMPLANT

CROSS-REFERENCE TO RELATED APPLICATIONS

The present application is a continuation-in-part U.S. application Ser. No. 14/825,082, filed on Aug. 12, 2015, which claims the benefit of U.S. Provisional Application No. 62/284,398, to which U.S. Design Application No. 29/474,342, filed Aug. 12, 2014 (the '342 application), was converted in accordance with the Request for Conversion to a Provisional Application under 37 C.F.R. 1.53(c)(2) filed Apr. 22, 2015, in the '342 application, which was granted on Aug. 17, 2015. The '342 application and the U.S. Provisional Application to which it was converted are hereby incorporated by reference herein in their entireties.

FIELD

This present disclosure relates generally to medical implants and, more particularly, to orthopedic and podiatry implants for use in a joint fusion (including fibrous union or even non-union) of the proximal or distal interphalangeal (PIP or DIP, respectively) joint of the toes. The present disclosure also relates to an interphalangeal fusion implant which provides for a stable relationship between the two phalanges, such as the proximal phalange and the intermediate phalange, which exists at the proximal interphalangeal joint.

BACKGROUND

Hammer toe is a deformity of the toe that affects the alignment of the bones adjacent to the proximal interphalangeal (PIP) joint or distal interphalangaeal (DIP) joint. Digital deformities of the fingers and toes are some of the most common conditions encountered by extremity specialists. These digital deformities can cause pain and lead to difficulty in walking, grasping or holding items and even wearing shoes. Examples of such deformities are popularly known as mallet finger, jersey finger, hammertoe, claw toe and mallet toe, as well as many others, indicative of several different pathologies.

Depending on the severity of the deformity, surgery may be required to correct the deformity by fusing one or both of the joints together, including the proximal interphalangeal (PIP) joint and the distal interphalangeal (DIP) joint. In order to prevent recurrence of the deformity and ensure the success of the surgical procedure, a proximal interphalangeal (PIP) joint or distal interphalangeal (DIP) joint arthrodesis is typically performed. The most commonly used hammertoe procedure is that which was described by Post in 1895 and is referred to today as the Post Arthroplasty or Post Procedure. It involves resecting (removing) the knuckle of the toe at the level of the proximal interphalangeal joint (PIPJ). This joint is the joint closest to the point where the toe attaches to the foot. Typically the Post Procedure will be performed in conjunction with a tendon release on the top (extensor surface) of the foot. The combination of these two procedures results in a toe that will lay flat avoiding direct pressure from the shoe. In the case of a mallet toe or claw toe, the Post Procedure may be performed with or without the tendon lengthening. The PIPJ is aligned with the rest of the toe in a corrected anatomical position and maintained in place by the use of a 0.045 or 0.062 inch diameter Kirschner wire (K-wire) driven across the joint. Initially, the K-wire is placed from the PIPJ through the tip or end of the toe. It is then driven in retrograde fashion into the proximal phalanx. The exposed K-wire is bent to an angle greater than 90 degrees, and the bent portion which is external of the body is cut. Normally a plastic or polymeric ball is placed over the exposed end of the K-wire to protect the patient. The K-wire normally remains in the foot of the patient until the PIP and/or DIP joints are fused in approximately 6 to 12 weeks. This conventional treatment has several drawbacks such as preventing the patient from wearing closed shoes while the K-wire is in place, and the plastic or polymeric ball may snag on some object due to it extending from the tip of the toe resulting in substantial pain for the patient.

There is a fairly high incidence of malunion (healing crooked) with traditional K-wire fixation. Other possible drawbacks of K-wire reported in the literature is that it must be removed which may cause additional pain for the patient along with the reported concern of infection at the insertion point of the toe.

Yet other conventional implants, in lieu of a K-wire, include threaded screws that are disposed within the adjacent bones of a patient's foot or nitinol implants that expand due to the rising temperature of the implant to provide outward forces on the surrounding bone when installed. However, the temperature sensitive material of a nitinol implant may result in the implant deploying or expanding prior to being installed, which requires a new implant to be used. Recently, PEEK polymer implants have been used to accomplish the same fixation of the deformity but these implants do not create bone ingrowth or upgrowth on the implant, which may lead to rotation of the implant and not accomplish the fusion required to correct the deformity over time for the patient. Accordingly, an improved implant for treating toe deformities is desirable.

SUMMARY

In one or more embodiments, an interphalangeal toe implant for deformity correction of a hammer toe, a mallet toe, a claw toe, or an arthritic toe condition comprises an implant body. The implant body can have a threaded proximal end section for fixation to a first bone portion, and a distal end section with fixation features for fixing the implant body to a second bone portion. The implant body can comprise polyetheretherketone (PEEK) and can have an osteoconductive coating that can comprise titanium plasma and/or hydroxyapatite (Harp). The osteoconductive coating can provide a surface for promoting bone growth when the implant is implanted in the first and second bone portions. The implant body can be substantially radiolucent such that edges of the two fused bones can be viewed under fluoroscopy even when the implant is fully implanted.

In one or more embodiments, an interphalangeal toe implant for correction of a deformity of the toe comprises an implant body. The implant body can have a threaded proximal end section for fixation to a first bone portion, and a distal end section with fixation features for fixing the implant body to a second bone portion. The implant body can comprise a medical-grade thermoplastic or polymer. The implant body can have an osteoconductive coating. To enhance the radiolucent property, the implant body may be coated with the osteoconductive coating at two ends of the implant body, leaving a middle region of the implant body uncoated.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements. As used herein, various embodiments can mean one, some, or all embodiments.

FIG. 1 is a perspective view of a titanium plasma coated medical grade thermoplastic or polymer proximal interphalangeal or distal interphalangeal toe implant used for deformity correction of hammer toe, mallet toe or claw toe, according to one or more embodiments of the disclosed subject matter.

FIG. 2 is a side view of the implant shown in FIG. 1, according to one or more embodiments of the disclosed subject matter.

FIG. 3 is another side view of the implant shown in FIG. 1, according to one or more embodiments of the disclosed subject matter.

FIG. 4 is a proximal end view of the implant shown in FIG. 1, according to one or more embodiments of the disclosed subject matter.

FIG. 5 is a distal end view of the implant shown in FIG. 1, according to one or more embodiments of the disclosed subject matter.

FIG. 6 is a side view of an angled implant, according to one or more embodiments of the disclosed subject matter.

FIG. 7 is a distal end view of the angled implant shown in FIG. 6, according to one or more embodiments of the disclosed subject matter.

FIG. 8 is a proximal end view of the angled implant shown in FIG. 6, according to one or more embodiments of the disclosed subject matter.

FIG. 9 is a bottom view of the angled implant shown in FIG. 6, according to one or more embodiments of the disclosed subject matter.

FIG. 10 is a cross sectional view of the angled implant shown in FIG. 6, according to one or more embodiments of the disclosed subject matter.

FIG. 11 is a side view of an implant, according to one or more embodiments of the disclosed subject matter.

FIG. 12 is a distal end view of the implant shown in FIG. 11, according to one or more embodiments of the disclosed subject matter.

FIG. 13 is a proximal end view of the implant shown in FIG. 11, according to one or more embodiments of the disclosed subject matter.

FIG. 14 is a partial distal end view of the implant shown in FIG. 11, according to one or more embodiments of the disclosed subject matter.

FIG. 15 is a partial side view of the implant shown in FIG. 11, according to one or more embodiments of the disclosed subject matter.

FIG. 16 is a partial side view of the implant shown in FIG. 11, according to one or more embodiments of the disclosed subject matter.

DETAILED DESCRIPTION

Figure 17A:
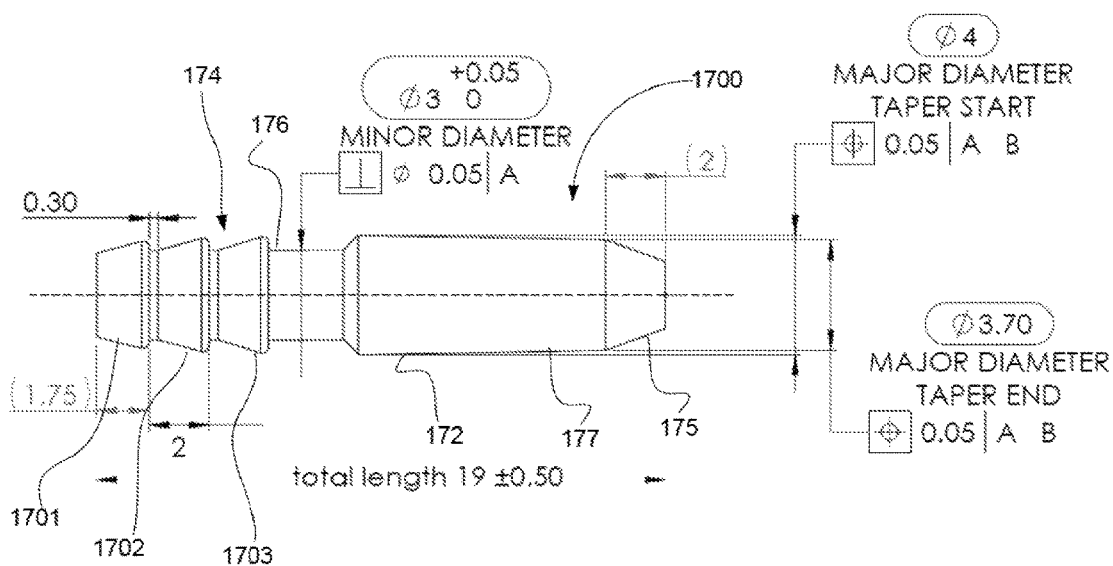
FIG. 17A is a side view of an embodiment of an implant according to the disclosed subject matter.

By the present disclosure there is provided a medical grade thermoplastic or polymer proximal interphalangeal or distal interphalangeal toe implant having an osteoconductive coating. In some embodiments, the osteoconductive coating is titanium plasma and/or hydroxyapatite (HAp).

The present application includes examples showing how the present invention overcomes possible deficiencies and complications resulting from the use of conventional hammer toe, mallet toe or claw toe implants made out of K-wires, stainless steel, titanium, nitinol implants or non-coated polymer implants.

For example, certain conventional implants for proximal interphalangeal (PIP) and distal interphalangeal (PIP) toe procedures studied by the applicants have been focused merely on obtaining compression at the joint to hold the joint together while waiting the 6-8 weeks until fusion takes place. However, such implants may toggle and rotate (e.g., if the joint interface is not the best bone), thus creating problems. Therefore, there is a need for a proximal interphalangeal or distal interphalangeal toe implant that provides compression along with bone ingrowth on the stems of the implant to help eliminate movement.

In one or more embodiments, a coated medical grade thermoplastic or polymer proximal interphalangeal or distal interphalangeal toe implant used for deformity correction of hammer toe, mallet toe or claw toe comprises materials shown to be osteoconductive. Osteoconductivity is the process by which bone grows on a surface (e.g., new bone growth that is perpetuated by the native bone). The coated medical grade thermoplastic or polymer proximal interphalangeal or distal interphalangeal toe implant may come in a variety of sizes depending on the required deformity correction. In one or more embodiments, at least one surface of the toe implant is coated with one or more osteoconductive materials or compounds such as, for example, titanium plasma and/or hydroxyapatite (HAp). Thus, a portion of the surface of the implant may remain uncoated, which can provide desirable attributes described below.

In some embodiments, medical grade materials/polymers are used to replicate bone as an implant. Medically accepted materials/polymers including but not limited to polyetheretherketone (PEEK), polyehterketoneketone (PEKK), Carbon Fiber-PEKK combination, titanium plasma coated PEEK and other polymer composite material have passed the review of the U.S. Food and Drug Administration (FDA), allowing them to be used in medical implants. Some of these polymer composites have been shown to be osteoconductive. In some embodiments, one or more surfaces are coated with an osteoconductive material or compound such as, for example, HAp. Some such medical grade polymers have met the stringent manufacturing guidelines ISO 10993 biocompatibility testing, along with other accepted manufacturing and biocompatibility guidelines. Medical grade polymers have the advantage of being able to be molded into any shape or design desired, such as, for example, those shown in FIGS. 1-5, 7-14, and 17-19 and discussed below.

Embodiments comprising an osteoconductive coating such as titanium plasma and/or HAp have the advantage of providing an implant that offers osteoconductivity with ingrowth or upgrowth on the implant. In contrast to embodiments of the present disclosure, plain, non-coated PEEK implants, for example, promote no bone upgrowth or ongrowth. However, an implant that retains at least a portion of the implant body uncoated provides improved radiolucent property of the implant, providing a view of the bone edges that have been fused under fluoroscopy.

For purposes of promoting an understanding of the principles of the present disclosure, reference will now be made to the examples illustrated in the drawings and described in the following written specification. It is understood that no limitation to the scope of the present disclosure is thereby intended. It is further understood that the present disclosure includes any alteration and modifications to the illustrated examples and includes further applications of the principles disclosed herein as would normally occur to one skilled in the art to which this disclosure pertains.

FIGS. 1-5 depict various views of embodiments of a titanium plasma coated medical grade thermoplastic or polymer proximal interphalangeal or distal interphalangeal toe implant used for deformity correction of hammer toe, mallet toe and claw toe.

FIG. 1 is a perspective view of a titanium plasma coated medical grade thermoplastic or polymer proximal interphalangeal or distal interphalangeal toe implant 100 used for deformity correction of hammer toe, mallet toe or claw toe, according to one or more embodiments of the disclosed subject matter. Implant 100 comprises a threaded proximal end section 102, a central section 106, and a distal end section 104. Threaded proximal end section 102 has threads for fixation to a first bone portion and distal end section 104 has fixation features, such as splines, for fixing the implant 100 to a second bone portion.

Implant 100 comprises a medical-grade thermoplastic or polymer such as, for example, PEEK, and is coated with an osteoconductive coating comprising titanium plasma. In some embodiments, the coating is between 125 microns and 500 microns thick. Alternatively or additionally, in some embodiments the osteoconductive coating comprises HAp.

In some embodiments, implant 100 includes one or more built-in conventional metal/alloy markers (not shown) located distally, proximally and/or in the middle of implant 100, to render the implant radiolucent. PEEK is translucent and the tantalum marker would allow it to be viewed under fluoroscopy. For example, markers can be included in implant 100 at sections 102, 104, and/or 106. The markers can comprise tantalum metal/alloy or any other metal/alloy viewable under fluoroscopy. The middle section 106 can remain uncoated with titanium, further increasing radiolucency under fluoroscopy.

In some embodiments, implant 100 is not cannulated (i.e., it is solid). Alternatively, implant 100 can be cannulated as shown, for example, in FIGS. 4 and 5, and described below. In such embodiments, the cannula diameter can be between 0.035 and 0.065 inches.

FIGS. 2 and 3 are side views of implant 100 shown in FIG. 1, according to one or more embodiments of the disclosed subject matter. As shown in FIGS. 2 and 3, implant 100 is straight. Alternatively, in some embodiments, implant 100 can be angled as shown, for example, in FIGS. 6-10.

FIG. 4 is a proximal end view of implant 100 shown in FIG. 1, according to one or more embodiments of the disclosed subject matter. As discussed above, implant 100 can be cannulated and include a proximal end cannula opening 402.

FIG. 5 is a distal end view of implant 100 shown in FIG. 1, according to one or more embodiments of the disclosed subject matter. As discussed above, implant 100 can be cannulated and include a distal end cannula opening 502.

FIGS. 6-10 depict various views of an angled implant, according to one or more embodiments of the disclosed subject matter.

FIG. 6 is a side view of an angled implant 600, according to one or more embodiments of the disclosed subject matter. Implant 600 comprises a threaded proximal end section 602, a central section 606, and a distal end section 604. Threaded proximal end section 602 has threads for fixation to a first bone portion and distal end section 604 has fixation features for fixing the implant 600 to a second bone portion. Central section 606 central is shaped such that threaded proximal end section 602 is oriented at a predetermined angle to distal end section 604 of the implant 600.

As shown, implant 600 is 3.5 mm diameter×26 mm long with a 10° angulation. In other embodiments, implant 600 can be provided in different sizes/configurations depending on the specific anatomy and desired correction. For example, the angulation can be between 0° (straight) and 25°.

Implant 600 comprises a medical-grade thermoplastic or polymer such as, for example, PEEK, and is coated with an osteoconductive coating comprising titanium plasma and/or hydroxyapatite (HAp). In some embodiments, the coating is between 125 microns and 500 microns thick. The osteoconductive (e.g., titanium plasma and/or HAp) coating promotes bone upgrowth on implant 600.

In some embodiments, implant 600 includes one or more built-in conventional metal/alloy markers (not shown) located distally, proximally and/or in the middle of implant 600, to render the implant radiolucent. PEEK is translucent and the tantalum marker allows it to be viewed under fluoroscopy. For example, markers can be included in implant 600 at sections 602, 604, and/or 606. The markers can comprise tantalum metal/alloy or any other metal/alloy viewable under fluoroscopy.

In some embodiments, implant 600 is not cannulated (i.e., it is solid). Alternatively, implant 600 can be cannulated as shown, for example, in FIGS. 7, 8, and 10, and described below. In such embodiments, the cannula diameter can be between 0.035 and 0.065 inches.

FIG. 7 is a distal end view of angled implant 600 shown in FIG. 6, according to one or more embodiments of the disclosed subject matter. As discussed above, implant 600 can be cannulated and include a distal end cannula opening 702.

FIG. 8 is a proximal end view of angled implant 600 shown in FIG. 6, according to one or more embodiments of the disclosed subject matter. As discussed above, implant 600 can be cannulated and include a proximal end cannula opening 802.

FIG. 9 is a bottom view of angled implant 600 shown in FIG. 6, according to one or more embodiments of the disclosed subject matter. A cross sectional view of implant 600 at plane 902 is shown in FIG. 10.

FIG. 10 is a cross sectional view of angled implant 600 shown in FIG. 6, according to one or more embodiments of the disclosed subject matter. As shown in FIG. 10, implant 600 is cannulated and includes a cannula 1002. In some embodiments, cannula 1002 can have a diameter between 0.035 and 0.062 inches.

FIGS. 11-16 depict various views of a straight implant according to one or more embodiments of the disclosed subject matter.

FIG. 11 is a side view of an implant according to one or more embodiments of the disclosed subject matter. Implant 1100 comprises a threaded proximal end section 1102, a central section 1106, and a distal end section 1104. Threaded proximal end section 1102 has threads for fixation to a first bone portion and distal end section 1104 has fixation features for fixing the implant 1100 to a second bone portion.

As shown, implant 1100 is 3.5 mm×22 mm, with a cannula diameter of 0.065 inches. In other embodiments, implant 1100 can be provided in different sizes/configurations depending on the specific anatomy and desired correction. For example, the cannula diameter can be between 0.035 and 0.065 inches.

Implant 1100 comprises a medical-grade thermoplastic or polymer such as PEEK, and is coated with an osteoconductive coating comprising titanium plasma and/or hydroxyapatite (HAp). In some embodiments, the coating is between 125 microns and 500 microns thick.

In some embodiments, implant 1100 includes one or more conventional built-in metal/alloy markers (not shown) located distally, proximally and/or in the middle of implant 1100, to render it radiolucent. PEEK is translucent and the tantalum marker allows it to be viewed under fluoroscopy. For example, markers can be included in implant 1100 at sections 1102, 1104, and/or 1106. The markers can comprise tantalum metal/alloy or any other metal/alloy viewable under fluoroscopy.

In some embodiments, implant 1100 is not cannulated (i.e., solid).

FIG. 12 is a distal end view of implant 1100 shown in FIG. 11, according to one or more embodiments of the disclosed subject matter. As discussed above, implant 1100 can be cannulated and include a distal end cannula opening 1202, as shown in FIG. 12.

FIG. 13 is a proximal end view of implant 1100 shown in FIG. 11, according to one or more embodiments of the disclosed subject matter. As discussed above, implant 1100 can be cannulated and include a proximal end cannula opening 1202, as shown in FIG. 13.

FIG. 14 is a partial distal end view of implant 1100 shown in FIG. 11, according to one or more embodiments of the disclosed subject matter. Distal end section 1104 includes fixation features 1402 for fixing the implant 1100 to a portion of bone.

FIG. 15 is a partial side view of implant 1100 shown in FIG. 11, according to one or more embodiments of the disclosed subject matter. Threaded proximal end section 1102 includes threads 1502 for fixation to a portion of bone.

FIG. 16 is a partial side view of implant 1100 shown in FIG. 11, according to one or more embodiments of the disclosed subject matter. Distal end section 1104 includes fixation features 1602 for fixing the implant 1100 to a portion of bone.

Figure 17B:
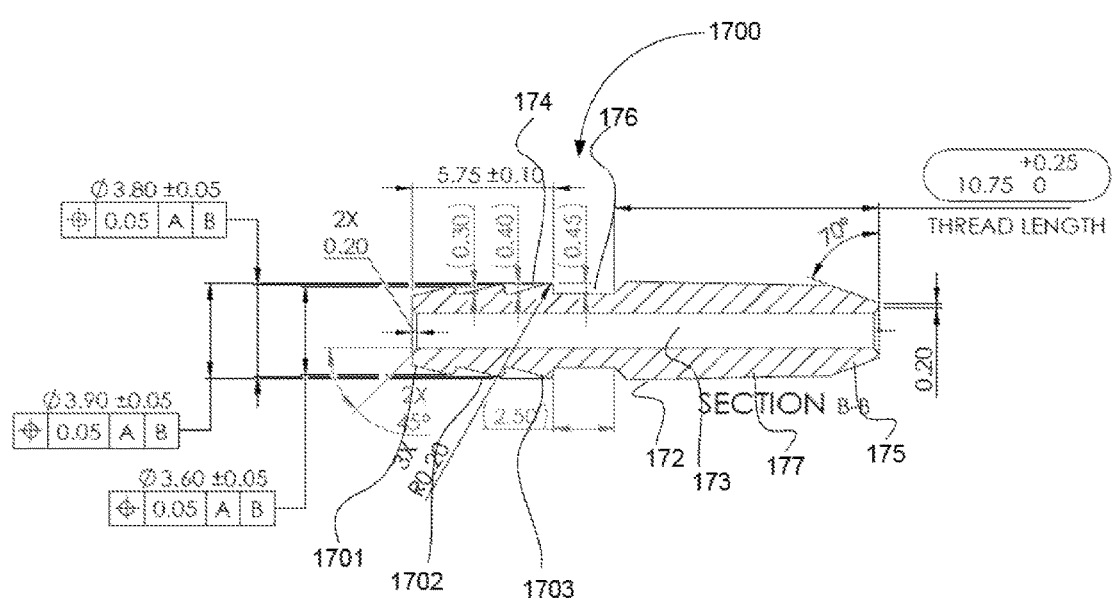
FIG. 17B is a cross-sectional view of an embodiment of an implant according to the disclosed subject matter.

FIGS. 17A and 17B illustrate a view of another embodiment of the implant. These figures include dimensions in millimeters and degrees showing a particular embodiment, however, the disclosed subject matter includes embodiments with dimensions that differ from those shown and thus, the disclosed subject matter as a whole is not limited to the specific dimensions shown.

The implant 1700 has a hollow body (the central cavity 173 shown in FIG. 17B) with three sections. The distal section 174 has three barbs of increasing size, as shown in FIGS. 17A and 17B. The first barb 1701 has the lowest rise from the central cavity, the second barb 1702 has a higher rise, and the third barb 1703 has the highest rise. The rise can be characterized as the outermost diameter of the barb. In alternative embodiments, the barbs can differ in terms of number, the arrangements of the rises. In embodiments, the rises of two or more barbs can be equal. For example, the first rise 1701 can be smaller while the other two 1702 and 103 can be larger and identical in outer diameter. In an embodiment, the outermost diameter of the first barb is 3.6 mm (with a tolerance of +/−0.05 mm); the outermost diameter of the second barb is 3.8 mm (with the same tolerance); and the diameter of the third barb is 3.9 mm (with the same tolerance).

The progressive increasing (or ramping) of the barb outer diameter has shown advantages when the implant is inserted into a bone cavity. Bones observed before and after insertion of the implant have shown less damage to marrow and internal bone structure with the disclosed increasing barb diameter as compared to an implant with uniformly sized barbs. When a barb is pressed against the outer wall of the bone cavity, it compresses the internal material and structure in the bone. The compression occurs incrementally as each barb passes through the bone cavity, thereby compressing the side wall of the bone cavity in stages. Further, the disclosed arrangement of barbs shows increased retention strength as compared to uniformly sized barbs. The tissue in the bone cavity is only compressed to a maximum extent once, and thus recovers more fully to its original size and position to retain the barb.

This concept applies to embodiments with more or less than three barbs, such as the embodiment of FIG. 6. Thus, an implant with any number of barbs which are arranged with outer diameters increasing from the distal end of the implant toward the central region is contemplated by the present disclosure.

Figure 18A:
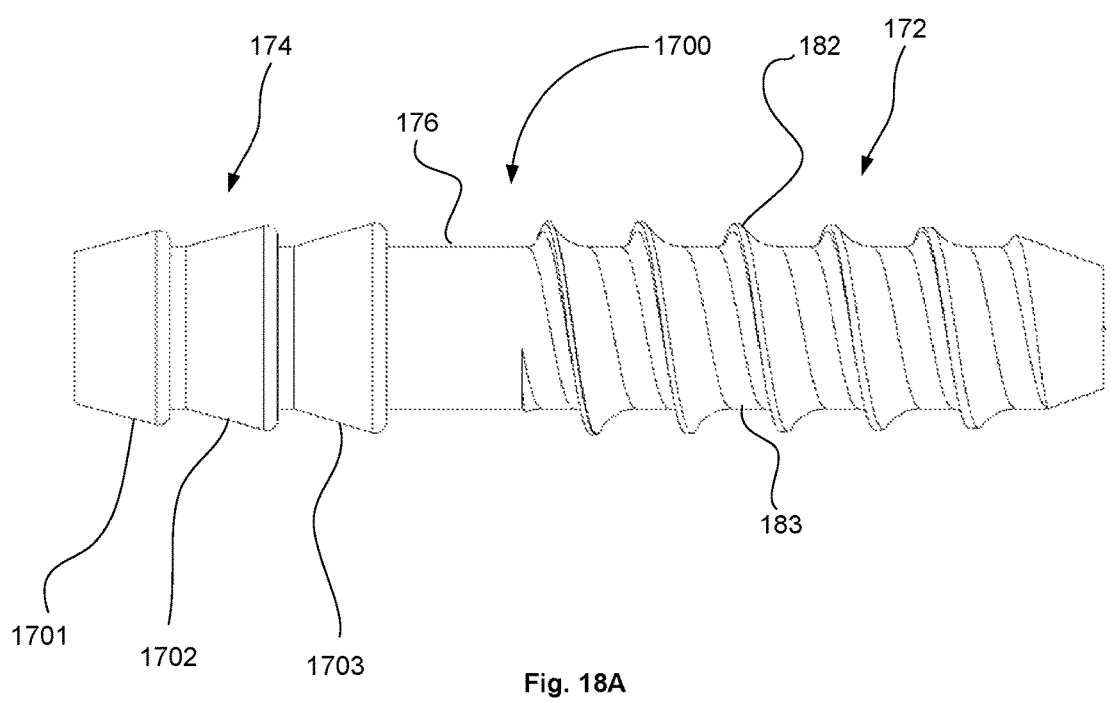
FIG. 18A is a side view of an embodiment of an implant according to the disclosed subject matter.
Figure 18B:
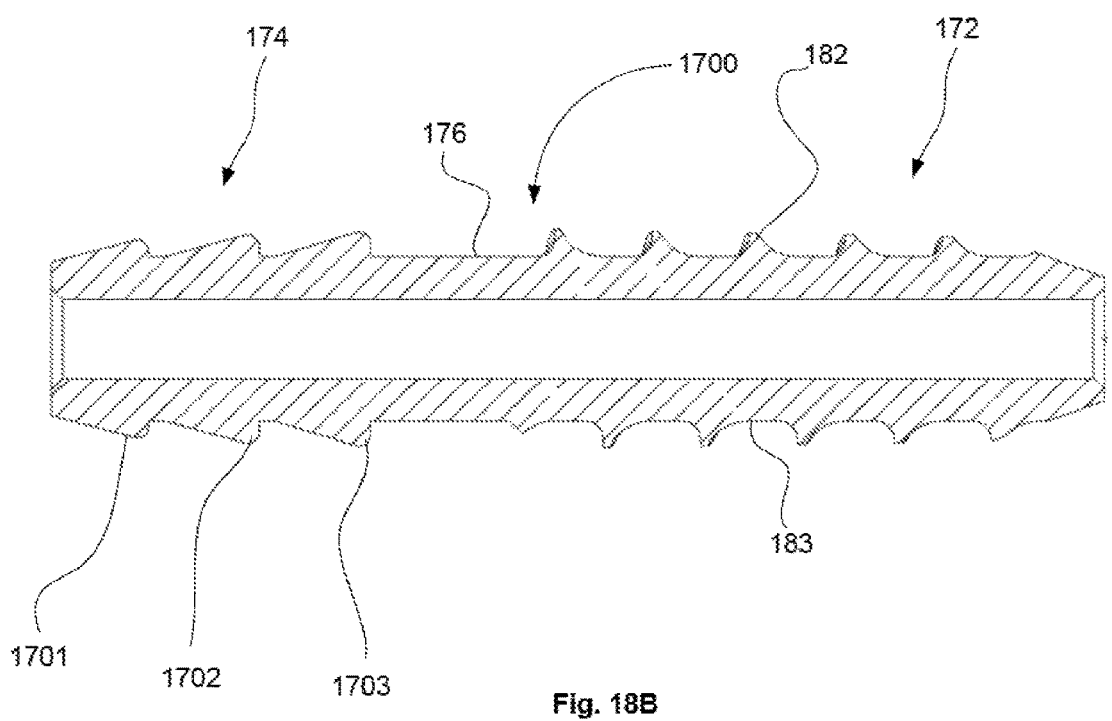
FIG. 18B is a cross-sectional view of an embodiment of an implant according to the disclosed subject matter.

Referring to FIG. 17B, the proximal portion 172 of the implant 1700 includes a dual-tapered portion. The first taper 175 extends from the proximal end of the proximal portion for 2 mm in an embodiment. Then, the second taper 177 continues for 8.75 mm. The first taper 175 may form an angle of 70 degrees from vertical, as shown in FIG. 17B. Although no threads are shown on proximal portion 172, in embodiments threads 182 may be present, as shown in FIGS. 18A-B. As shown in FIGS. 17B and 18B, embodiments of implant 1700 include a monolithic body.

Referring to FIG. 18A, threads 182 are formed on the proximal portion 172. The threads 182 extend radial away from a tubular section 183 and have an outer diameter that increases progressively from the proximal end toward the central portion 176. Thus, the outermost diameter of the proximal portion 172 (formed by the outermost surface of threads 182) increases from the proximal end toward the central portion 176. This progressive increase in the outer diameter of the threads provides advantages as noted above with respect to the barbs 1701, 1702, and 1703. As seen in FIG. 18A and in the cross-section view in FIG. 18B, the central portion 176 does not have any fixation features and has a cylindrical outer surface that extends continuously from the proximal portion 172 to the distal portion 174.

In an embodiment, the tubular section 183 has an outer diameter that is constant, rather than increasing progressively like the threads 182. In another embodiment, the tubular section 183 is itself tapered and its outer diameter increases progressively from the proximal end toward the central portion 176.

In an embodiment, the entirety of the external surface of implant 1700 is coated with a osteoconductive coating. As noted above, a portion of the implant 1700 may remain uncoated to provide improved radiolucency under fluoroscopy. In an embodiment, the central portion 176 is not coated, while portions 172 and 174 are coated. Of course, this coating arrangement also applies to FIGS. 18A-B, where portions 174 and threaded portion 182 can be coated, while the central portion 176 remains uncoated. In an embodiment, the central portion 176 is coated with an osteoconductive coating that is radiolucent while the rest of the implant is coated with a coating that is less radiolucent. In some embodiments, the entirety of the implant is coated with an osteoconductive coating that is radiolucent, thus making the coated implant radiolucent.

By leaving the central portion 176 uncoated, the radiolucency of the implant is increased in the region where the two bones being fused are expected to come together, while the distal portion and the proximal portion, coated with the osteoconductive coating, provide a compatible surface for bone growth. The improved radiolucency enables the clinician to observe the bone edges 191 and 192 under fluoroscopy during the procedure and/or at the conclusion, to ensure that the edges are in contact or at a position suitable for fusion of the two bone edges, as shown in FIG. 19.

Figure 19:
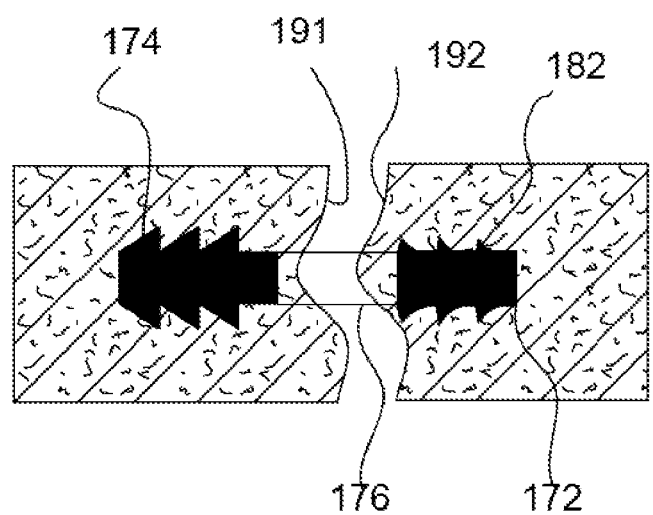
FIG. 19 is a schematic view of an implant used to fuse two bones according to the disclosed subject matter.

FIG. 19 represents a schematic of a fluoroscopy view that a clinician would observe when the central portion 176 is uncoated, while portions 172 and 174 are coated with an osteoconductive coating that impedes radiolucency. The improved radiolucency of the central portion 176 enables the clinician to monitor the fusion of the two bone edges over time, such as after 4-6 weeks, to observe and verify whether bone fusion is taking place. Because the region of interest where the bones are supposed to be fusing is not obscured by the implant, due to its radiolucency, it is typically possible to verify bone growth with a single fluoroscopic view. Conversely, an implant that is not radiolucent can obscure the bone fusion, making it more difficult for the clinician to ascertain the patient's progress.

A method of using an implant according to one or more embodiments of the disclosed subject matter will now be described.

Initially, the surgeon makes an incision over the dorsal aspect of the distal interphalangeal joint (DIP) or proximal interphalangeal joint (PIP) of the toes. Standard soft tissue releases are performed as necessary. The joint dissection and access should provide complete visualization of the articular surfaces of the middle and proximal phalanges of the DIP or PIP joints. The surgeon then prepares the joint surface of both the proximal and middle phalanges.

When using a solid implant (i.e., an implant without cannulation), the surgeon drills with the appropriate size drill bit, both sides of the DIP or PIP joints to the required depth. Surgeon then taps, if desirable, with the appropriate size tap both sides of the DIP or PIP joint to the required depth. Once both sides of the DIP or PIP joints are prepared properly, the surgeon then inserts the proximal portion of the implant into the proximal side of the joint either by hand or with the recommended instrument, to the recommended depth. Surgeon then distracts the joint distally, to pressfit the distal end of the implant into the predrilled/tapped hole of the DIP or PIP joint.

When using cannulated implants, after preparing the joint surface, the surgeon places a guide wire (e.g., from 0.035 up to 0.062 inches in diameter) into the proximal phalanx along its central axis, to the recommended depth. The surgeon then verifies proper positioning of the guide wire with AP (Anterior/Posterior) and Lateral (Medial/Lateral) fluoroscopic views. The surgeon then uses the recommended cannulated drill bit to predrill over the guide wire to the recommended depth. The surgeon then taps the drilled hole, if desirable, with the appropriate size tap to the recommended depth. The surgeon then removes the guide wire proximally to perform the same procedure to prepare the distal side of the joint.

The cannulated implant is then placed over the guide wire still in position distally. The surgeon, either by hand or with the recommended instrument, advances the cannulated implant over the guide wire into position in the distal end of the joint to the recommended position.

The guide wire is then advanced forward antegrade out the end of the toe, under the toe nail, so that its proximal end is flush with the implant. The surgeon then distracts the DIP or PIP joint in order to insert the proximal portion of the implant into the prepared joint proximally. The implant is pressfit or placed into the proximal portion of the joint to the recommended position.

The surgeon may remove the guide wire or advance the guide wire back through the cannulated implant past the DIP or PIP joint, to address fixation at the metatarsophalangeal (MTP) joint of the toe.

Embodiments of the present disclosure can be used for primary/revision of claw toe, hammer toe, or mallet toe deformity. Embodiments can be used for angular correction of deformities, arthritic conditions of lesser toes (traumatic/rheumatologic), and/or salvage of failed prior surgeries to lesser toes.

In the embodiments shown and described, a coated medical grade thermoplastic or polymer proximal interphalangeal or distal interphalangeal toe implant can be coated with a titanium plasma and/or hydroxyapatite (HAp) osteoconductive coating, can be provided in various sizes, cannulated or solid, angled or straight, with or without fluoroscopy markers, depending on the amount of correction required to address the deformity.

Although some embodiments herein have been described with respect to titanium plasma coated implants, embodiments of the disclosed subject matter are not limited thereto. Rather, embodiments can include implants coated with other osteoconductive coatings such as HAp.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, titanium plasma coated medical grade thermoplastic or polymer proximal and distal interphalangeal toe implant. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicant intends to embrace all such alternatives, modifications, equivalents, and variations that are within the spirit and scope of the present invention.

The invention claimed is:

1. An interphalangeal toe implant for deformity correction of a hammer toe, a mallet toe, a claw toe, or an arthritic toe condition, the implant comprising:
a monolithic body including a threaded proximal end section, at a proximal end of the implant, for fixation to a first bone portion, a distal end section, at a distal end of the implant, having fixation features for fixing the monolithic body to a second bone portion, and a central portion, devoid of threads and fixation features, rigidly connecting the proximal end section and the distal end section, wherein the monolithic body comprises polyetheretherketone (PEEK); and an osteoconductive coating applied to the proximal end section and the distal end section, wherein the osteoconductive coating provides a surface for promoting bone growth when the implant is implanted in the first and second bone portions, and the central portion of the monolithic body does not have any osteoconductive coating applied, such that the central portion is radiolucent after the osteoconductive coating is applied to the proximal end section and the distal end section.

2. The implant of claim 1, wherein the osteoconductive coating comprises titanium plasma.

3. The implant of claim 1, wherein the monolithic body is not cannulated.

4. The implant of claim 1, wherein the monolithic body is cannulated.

5. The implant of claim 1, wherein the central portion has a shape that causes the proximal end section of the monolithic body to be rigidly oriented at a predetermined angle to the distal end section of the monolithic body.

6. The implant of claim 5, wherein the predetermined angle is a non-zero angle for performing an angular correction of a deformity of the toe.

7. The implant according to claim 1, wherein the distal end section includes a plurality of barbs, each having a respective outer diameter, and the respective outer diameters of the plurality of barbs increase from the distal end of the implant toward the proximal end of the implant.

8. The implant according to claim 7, wherein the proximal end section includes threads, and the outer diameter of the threads increases from the proximal end of the implant toward the central portion.

9. The implant according to claim 1, wherein the central portion includes a cylindrical outer surface that extends continuously from the proximal end section to the distal end section.

10. An interphalangeal toe implant for deformity correction of a hammer toe, a mallet toe, a claw toe, or an arthritic toe condition, the implant comprising:

a monolithic body made of polyetheretherketone (PEEK), including a proximal end section, at a proximal end of the implant, for fixation to a first bone portion, a distal end section, at a distal end of the implant, with fixation features for fixing the monolithic body to a second bone portion, and a central portion rigidly connecting the proximal end section and the distal end section; and an osteoconductive coating applied to the proximal end section and the distal end section, wherein the osteoconductive coating provides a surface for promoting bone growth when the implant is implanted in the first and second bone portions, and the central portion of the monolithic body does not have any fixation features and does not have any osteoconductive coating applied, such that the central portion is radiolucent after the osteoconductive coating is applied to the proximal end section and the distal end section.

11. The implant of claim 10, wherein the osteoconductive coating comprises titanium plasma.

12. The implant of claim 10, wherein the distal end section includes a plurality of barbs, each having a respective outer diameter, the respective outer diameters of the plurality of barbs increase from the distal end of the implant toward the proximal end of the implant, and the proximal end section includes a first taper at the proximal end of the implant extending for a first distance and a second taper extending from an end of the first taper.

13. The implant of claim 12, wherein the proximal end section includes threads, and the outer diameter of the threads increases from the proximal end of the implant toward the central portion.

14. The implant of claim 10, wherein the monolithic body has a central section shaped such that the proximal end section of the monolithic body is oriented at a predetermined non-zero angle to the distal end section of the monolithic body.

15. The implant according to claim 10, wherein the central portion includes a cylindrical outer surface that extends continuously from the proximal end section to the distal end section.

\* \* \* \* \*